United States Patent [19]
Kavka

[11] 3,954,805
[45] May 4, 1976

[54] PROCESS FOR PREPARING ZEARALENE TYPE COMPOUNDS

[75] Inventor: Frank Kavka, Terre Haute, Ind.

[73] Assignee: Commercial Solvents Corporation, Terre Haute, Ind.

[22] Filed: Mar. 25, 1975

[21] Appl. No.: 561,898

Related U.S. Application Data

[63] Continuation of Ser. No. 476,888, June 6, 1974, abandoned.

[52] U.S. Cl. ........................... 260/343.2 F; 424/279
[51] Int. Cl.² ........................................ C07D 313/00
[58] Field of Search ............................. 260/343.2 F

[56] References Cited
OTHER PUBLICATIONS

Yamamura et al., *J. Chem. Soc.*, pp. 2887–2889 (1968).

Yamamura et al., *Chemical Communications*, pp. 1049–1050 (1967).

Toda et al., *Chemical Communications*, pp. 919–920 (1969).

Toda et al., *Bulletion of the Chemical Society of Japan*, Vol. 46, pp. 264–266 (1972).

*Primary Examiner*—John M. Ford
*Attorney, Agent, or Firm*—Morton, Bernard, Brown, Roberts & Sutherland

[57] ABSTRACT

Zearalene type compounds are prepared by treating zearalenone type compounds in a solvent selected from the group consisting of acetic anhydride, propionic anhydride, dioxane, ethyl acetate, ethyl ether, and tetrahydrofurane, under reducing conditions in the presence of reducing amounts of zinc and hydrogen halide.

14 Claims, No Drawings

PROCESS FOR PREPARING ZEARALENE TYPE COMPOUNDS

This is a continuation of application Ser. No. 476,888, filed June 6, 1974, now abandoned.

This invention is directed to a process for preparing zearalene type compounds having the following structural formula:

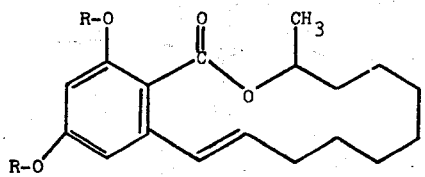

wherein R is selected from the group consisting of hydrogen; substituted and unsubstituted alkyl, e.g., containing from 1 to about 15 carbon atoms including lower alkyl such as methyl, ethyl, hexyl, etc., and cycloalkyl, particularly monocyclic alkyl of about 5 to 8 carbon atoms, such as cyclopentyl, cyclohexyl, methyl cyclohexyl, etc.; substituted or unsubstituted alkanoyl, generally containing 1 to about 25 or more carbon atoms including lower alkanoyl such as acetyl, propionyl, valeryl, etc.; substituted or unsubstituted aryl, for instance, monocyclic or bicyclic aryl containing about 6 to 15 carbon atoms or more, such as phenyl, tolyl, naphthyl, etc.; and aryl alkyl (that is an alkyl group having an aryl substituent thereon), wherein the aryl substituent may be monocyclic or bicyclic aryl containing about 6 to 15 carbon atoms or more and the alkyl group is generally lower alkyl, for example, 1 to about 6 carbon atoms, such as benzyl, bromobenzyl, benzoyl, tolyl methyl, and the like. Zearalene type compounds are disclosed in U.S. Pat. No. 3,239,341 to Hodge et al.

Zearalene type compounds produced by the process of this invention have been found to exhibit high antigonadotropicity and low uterotropicity. Antigonadotric agents are compounds which tend to shrink male genitalia and are often useful for suppression of testosterone production in males where that effect is desired, as, for example, in treating prostatic hypertrophy, either cancerous or benign. Prostatic hypertrophy is a condition of excessive growth of the prostate gland, and since this prostate gland growth is stimulated by testosterone, the administration of testosterone-suppressing drugs is sometimes employed as treatment.

Compounds useful as testosterone suppressants, in addition to exhibiting high antigonadotropin activity, preferably exhibit low uterotropin activity. Low uterotropin activity is an indicium of low estrogenicity, and low estrogenicity is desirable in testosterone suppressants to minimize any feminizing side effects that some testosterone-suppressing drugs exhibit. Thus, it is advantageous that the compounds produced by the process of the present invention exhibit both high antigonadotropicity and low uterotropicity.

Highly antiogonadotropic compounds have also been used in animal husbandry, for example, to synchronize procreation activities. The antigonadotropin activity is used to regulate the time at which an animal may come into heat and by such regulation procreation is controlled. Further, antigonadotropic agents are sometimes administered to dogs by hunters to prevent their dogs from coming into heat during the hunting season, and may be used by other animal owners or trainers to regulate procreation or to avoid estrus-related problems.

In accordance with the process of the present invention, a zearalenone type compound, having the structural formula

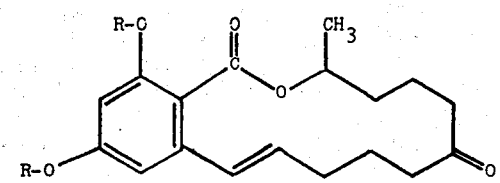

wherein R is as defined above, is reduced in a solvent selected from the group consisting of acetic anhydride, propionic anhydride, dioxane, ethyl acetate, ethyl ether and tetrahydrofurane, under reducing conditions in the presence of reducing amounts of zinc and a hydrogen halide selected from the group consisting of hydrogen chloride, hydrogen fluoride and hydrogen bromide, to convert the keto group of the zearalenone type compound to a methylene group to provide zearalene type compounds.

The zearalenone type compounds may be obtained by methods described in the art as, for example, described in U.S. Pat. Nos. 3,196,019 to Andrews et al., U.S. Pat. No. 3,624,144 to Wendler et al., U.S. Pat. No. 3,551,454 to Taub et al., and U.S. Pat. No. 3,551,455 to Girotra et al., all incorporated herein by reference, and as described in commonly assigned U.S. patent application Ser. No. 317,117, filed Dec. 21, 1972, now abandoned, also incorporated herein by reference.

The solvent is employed in solvent-providing amounts and, generally, these amounts will range from about 5 to 50, preferably from about 10 to 40, parts by weight of solvent to one part by weight of zearalenone type compound. Hydrogen halide is incorporated in the solvent in keto-reduction enhancing amounts to provide acidity to the solvent and hydrogen ions for the reduction and, generally, these amounts range from about 10 to 40, preferably from about 15 to 30, weight percent, based upon the weight of the solvent. Advantageously, the solvent is saturated with the hydrogen halide, and this provides a solvent containing about 30 wt. percent of hydrogen halide. The hydrogen halide used in the process is hydrogen chloride, hydrogen bromide, or hydrogen fluoride, with hydrogen chloride being preferred.

The zearalenone type compound, preferably, is first mixed with the hydrogen halide solvent, and then the zinc, in keto-reducing amounts, is advantageously added slowly to the mixture under agitation. Generally, from about 1 to about 20 or more, preferably from about 2.5 to about 8 parts by weight, of zinc is added per 1 part by weight of zearalenone-type compound.

The zinc may be either unactivated or activated, preferably activated, zinc in particle form. The particles may be of any commercially available size, but particles having a large surface area per volume are desirable, and usually a particle size of about 100 to about 400 mesh can be used.

Activated zinc is intended herein to mean zinc which has had, at least partially, zinc oxide removed from its surface. In reactions involving metallic powder, it is recognized that oxides may form on the surface of the powder and reduce the efficiency or effectiveness of the reaction. Generally, these oxides are removed, at least in part, by activation techniques. Any known activation technique may be used to prepare the zinc for use in the process of the present invention as long as the zinc is properly dried before use. In one such method, the zinc powder may be added to an acid such as dilute HCl, e.g. 2% HCl, and then separated and dried. Typical drying methods include, for example, repeated washings with water, then ethanol, then acetone, although other known methods may be as effective.

The mixture of the zearalenone type compound, hydrogen halide-containing solvent and zinc, is subjected to keto-reducing conditions which include temperatures sufficient to reduce to a keto group, but insufficient to cleave the non-aromatic ring component of the zearalenone compound. Generally, these temperatures will range from about −20° to +50°C., preferably from about −10° to +20°C., under ambient pressure conditions.

The reduction is conducted for a time sufficient to reduce the keto group, and this will generally range from about 5 minutes to 10 hours, depending upon the amount of zearalenone compound employed. The reaction is advantageously carried out under agitation, e.g. stirring, to assure that an efficient reaction proceeds to produce a good yield of a homogenous product.

The zearalene type compound reaction product may be removed from the reaction product mixture by known separation techniques, such as by solvent extraction, and identified, e.g. by thin layer chromatography. The zearalene type compound-containing product mixture may be neutralized before separation, e.g., with $Na_2CO_3$, although this is not necessary. The separated product may be purified by known techniques such as solvent dissolution - recrystallization techniques.

In one preferred embodiment of the present invention, when at least one R of the zearalenone type starting compound is hydrogen, e.g. 1'-trans-(10'S)-zearalenone, and the solvent is acetic anhydride or propionic anhydride, any hydroxyl group on the aromatic ring of the zearalenone compound is converted to an alkanoyl group corresponding to the particular anhydride employed. For instance, in the case of 1'-trans-(10'S)-zearalenone, the resulting product is dialkanoylzearalene, e.g. 2,4-diacetyl-1'-trans-(10'S)-zearalene. The alkanoyl products may be further treated under hydrolysis conditions to produce zearalene.

The hydrolysis conditions include any hydrolysis technique which does not detrimentally affect the remainder of the zearalene molecule. In one preferred method, the alkanoylzearalene is reacted with an esterification agent, e.g., a lower alkanol such as methanol, in the presence of catalytic amounts of an esterification catalyst to react with and replace the alkanoyl group with the hydroxyl group, the by-product being the ester of the alkanol employed. Suitable esterification catalysts include dry acids, e.g., acid halides such as hydrogen chloride, which is preferred, and alkali metal alkoxides, e.g., sodium methoxide. When employing acidic catalysts, e.g., hydrogen chloride, the hydrolysis is advantageously conducted under reflux temperature conditions, whereas, when employing alkali metal alkoxide, e.g., sodium methoxide, ambient (room temperature) conditions can be employed.

The following examples will serve to illustrate the process of the present invention, but are not to be considered limiting.

EXAMPLE I

35 Grams of zinc dust (Mallinckrodt, designated as analytical agent) were treated for 4 minutes with 100 ml. of 2% HCl. The resulting supernatant was decanted and washed 3 times with water, once with ethanol and then 3 times with acetone. It was then filtered from acetone and washed with anhydrous ether and dried under vacuum for 10 minutes at 90°C. to produce activated zinc.

3.2 Grams of 1'-trans-(10'S)-zearalenone (0.01 mole) were dissolved in 100 ml. of acetic anhydride which had been saturated with dry gaseous hydrogen chloride. The zearalenone was added to the saturated acetic anhydride while it was being maintained at about 0° to about −5°C. with a dry ice-acetone bath. The solution was kept at about 0° to about −5°C., while 35 grams of activated zinc were added in portions with stirring, over a ½ hour period. Then the mixture was maintained at about 3° to about 5°C. with an ice water bath for about 5 hours under agitation. The product mixture was filtered and the filtrate was washed with acetic anhydride and added to 1500 ml of an ice-water mixture. The mixture was neutralized with $NaHCO_3$ and extracted repeatedly with chloroform. The combined chloroform extracts were then dried with $Na_2SO_4$.

Column chromatography techniques were used to isolate the diacetylzearalene fractions of the product which were combined and analyzed. A yield of 92% (3.6 grams) was obtained. Nuclear Magnetic Resonance (NMR) and Infrared Spectrum tests verified that the product was diacetylzearalene. Elementary analysis established that 67.70 wt. % carbon (calculated to be 68.02%) and 7.42 wt. % hydrogen (calculated to be 7.27%) were present.

EXAMPLE II

A portion of the diacetylzearalene fractions obtained in Example I was hydrolyzed as follows:

About 3.1 grams of the diacetylzearalene were dissolved in a mixture of 20 ml. of absolute methanol and 20 ml. of 0.71 N sodium methoxide solution and stirred for 30 minutes at a temperature of about 25°C. The mixture was then diluted with 150 ml. of ice and water and neutralized with 20% HCl in the presence of $KH_2PO_4$. The product was extracted from the mixture with chloroform and ethyl acetate and combined and washed with 100 ml. of water and dried with $Na_2SO_4$. About 1.7 grams of light brown solid were obtained, which were recrystallized from water and methanol.

NMR spectrum established that two OH groups were present on the benzene ring portion of the molecule, indicating hydrolysis of the acetyl groups. The crystals were purified by column chromatography to give a crystalline product, zearalene, melting at 164°–165.5°. Elementary analysis established that 71.11% wt. % carbon (calculated to be 71.03%) and 8.13 wt. % hydrogen (calculated to be 7.95%) were present.

EXAMPLE III

140 Grams of zinc dust (Mallinckrodt, designated as analytical agent) were treated for 4 minutes with 400 ml. of 2% HCl, rinsed three times with 400 ml. of water, twice with 400 ml. of ethanol and three times with 400 ml. of acetone. It was then washed with anhydrous ether, separated and dried at 90°C. for about 12 minutes.

25.6 Grams of 1'-trans-(10'S)-zearalenone were dissolved in about 400 ml. of acetic anhydride which had been saturated with dry HCl at a temperature of about 5°C. (350 ml. of acetic anhydride was saturated with 149 grams of dry HCl to produce a volume of 400 ml.). 140 Grams of the activated zinc were added in portions to the acetic anhydride solution over a 1 hour period at about 0° to 5°C., under agitation. The resulting mixture was stirred at that temperature for about 1 hour after all the zinc had been added. The mixture was combined with 2 to 5 liters of ice water under agitation and neutralized with 173 grams of $Na_2CO_3$ to a pH of about 6. The product was extracted with three rinsings of chloroform, combined, washed with an 800 ml. water-$NaHCO_3$ solution, dried with $Na_2SO_4$ and evaporated to yield 36.5 grams of a light-yellow oil. The residue was dissolved in solvent and chromatographed. The product, 25.1 grams of diacetylzearalene, was produced with a yield of about 80%.

EXAMPLE IV

Diacetylzearalene was hydrolyzed as follows:

23.0 grams of diacetylzearalene of the type produced in Example III were dissolved in 460 ml. of methanol and 5.1 ml. of 9.08 N HCl in methanol were added. The solution was refluxed at a temperature of about 64°C., with stirring, for about 55 minutes. A thin layer chromatogram run on the product indicated that there was no presence of either diacetylzearalene or monoacetylzearalene.

The residue product was neutralized with 4.2 grams of $NaHCO_3$ and evaporated to dryness. It was then dissolved in ether and water, the layers which formed were separated and the organic layer was washed with water several times and dried with $Na_2SO_4$. The dried residue was subsequently dissolved in 90 ml. of hot benzene at about 75°C., and was allowed to crystallize under refrigeration to produce about 7.0 grams of zearalene having a melting point of about 164° to 165°C. The mother liquors were concentrated sequentially to produce, first, 6.6 grams melting at about 162.5° to 163.5°C. and then 0.7 grams melting at about 159.5° to 161.5°C. Thus, about 14.3 grams of zearalene product determined to be 1'-trans-(10'S)-zearalene were produced with a total yield of about 74%.

EXAMPLE V

Antigonadotropicity of 1'-trans-(10'S)-zearalene is exhibited by test results of a general pharmacological activity screen test performed on the compound by Endocrine Laboratories of Madison, Inc., Madison Wis. The compound was administered once daily for 14 days by oral administration. The test animals were intact male rats 21 days of age at the start of the test. Eight rats received no compound and two different dosages were each administered to groups of eight. The average results are shown in Table 1, below. Significant antigonadotropin activity is exhibited in the Table which shows that, after 14 days, the rats receiving 2.0 mg. per day of the compound had testes weighing, on the average, less than 50% the weight of the testes of the rats receiving no compound. Similarly significant weight differences are shown in ventral prostate and seminal vesicles weights.

Table 1

| Treatment with zearalene | | Control (0) | (0.5 mg) | (2.0 mg) |
| --- | --- | --- | --- | --- |
| Initial Body Weight | (gm) | 58 | 58 | 58 |
| Final Body Weight | (gm) | 146 | 139 | 129 |
| Testes | (mg) | 1525 | 1311 | 733 |
| Ventral Prostate | (mg) | 118.3 | 68.7 | 37.4 |
| Seminal Vesicles | (mg) | 47.7 | 30.0 | 23.4 |
| Levator Ani | (mg) | 71.3 | 51.6 | 46.5 |
| Spleen | (mg) | 671 | 598 | 569 |
| Adrenals | (mg) | 42.4 | 38.0 | 43.4 |
| Left Kidney | (mg) | 850 | 789 | 717 |
| Liver | (mg) | 9.2 | 8.2 | 8.6 |
| Thymus | (mg) | 563 | 475 | 375 |
| Thyroid | (mg) | 11.1 | 11.1 | 11.5 |
| Pit. | (mg) | 6.0 | 6.8 | 7.3 |

EXAMPLE VI

Relatively low uterotropicity of 1'-trans-(10'S)-zearalene is also exhibited by test results of the pharmacological activity screen test mentioned in Example V. The compound was given once daily for 14 days by oral administration. The test animals were intact female rats 30 days of age at the start of the test. Again, 24 rats were tested, eight received no compound, eight received 0.5 mg. and eight received 2.0 mg. The averaged results are shown in Table 2, below. As the Table shows, uterine weight differences are less than 15% between those of the control rats and those receiving 2.0 mg. of compound, suggesting low uterotropin activity. Also, no significant difference in ovarian weight is exhibited.

Table 2

| Treatment with zearalene | | Control (0) | (0.5 mg) | (2.0 mg) |
| --- | --- | --- | --- | --- |
| Initial Body Weight | (gm) | 90 | 91 | 91 |
| Final Body Weight | (gm) | 157 | 164 | 156 |
| Ovarian Weight | (mg) | 57.3 | 65.8 | 55.8 |
| Uterine Weight | (mg) | 242.2 | 231.2 | 210.7 |
| No. of Corpula Lutea | | 13 | 15 | 12 |
| Spleen | (mg) | 656 | 707 | 648 |
| Adrenals | (mg) | 50.5 | 56.8 | 58.5 |
| Left Kidney | (mg) | 927 | 971 | 923 |
| Liver | (mg) | 10.1 | 10.9 | 10.1 |
| Thymus | (mg) | 438 | 559 | 447 |
| Thyroid | (mg) | 14.5 | 15.6 | 15.4 |
| Pit. | (mg) | 9.6 | 10.6 | 11.1 |

EXAMPLES VII TO XI

The procedure of Example I is essentially repeated except a zearalenone having the formula

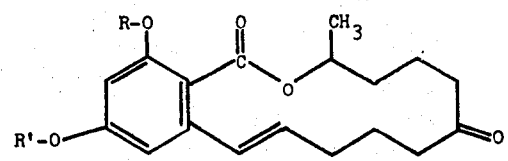

is employed in the solvents designated in Table I, to produce a zearalene having the formula

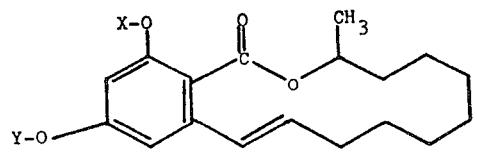

The values for R, R', X and Y for a given Example are set forth in Table 3.

Table 3

| Example | R | R' | X | Y | Solvent |
|---|---|---|---|---|---|
| VII | $CH_3$ | $CH_3$ | $CH_3$ | $CH_3$ | dioxane |
| VIII | benzyl | benzyl | benzyl | benzyl | ethyl acetate |
| IX | $-\overset{O}{\overset{\|}{C}}-CH_3$ | $-\overset{O}{\overset{\|}{C}}-CH_3$ | $-\overset{O}{\overset{\|}{C}}-CH_3$ | $-\overset{O}{\overset{\|}{C}}-CH_3$ | ethyl ether |
| X | H | H | H | H | tetrahydrofurane |
| XI | H | H | $-\overset{O}{\overset{\|}{C}}-CH_2-CH_3$ | $-\overset{O}{\overset{\|}{C}}-CH_2-CH_3$ | propionic anhydride |

The use of dioxane, ethyl acetate, ethyl ether or tetrahydrofurane, as solvents, obviates the use of a hydrolysis procedure when R or R' is H and the product desired is one where X or Y is H, since these solvents, as distinguished from the use of acetic or propionic anhydrides as solvents, do not react with the hydroxyl group on the aromatic ring during the reduction of the keto group. However, when using acetic anhydride as a solvent, a substantially greater yield of zearalene product is produced, even though the hydrolysis procedure is employed, as compared to that produced when using dioxane solvent when R or R' of the starting compound is H and it is desired that the corresponding components be the same in the product.

Various modifications or equivalents will be apparent to one skilled in the art, and may be made in the present invention without departing from the spirit or scope thereof, and is, therefore, to be understood that these modifications or equivalents are within the scope of the present invention.

It is claimed:

1. A process for preparing a zearalene type compound which comprises treating a zearalenone compound having the structural formula 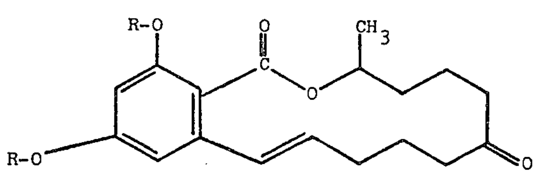 wherein R is selected from the group consisting of hydrogen, lower alkyl, monocyclic aryl and lower alkanoyl, in a solvent selected from the group consisting of dioxane, ethyl acetate, ethyl ether, tetrahydrofurane, acetic anhydride and propionic anhydride, under keto-reducing conditions in the presence of keto-reducing amounts of zinc and hydrogen halide selected from the group consisting of hydrogen fluoride, hydrogen bromide, and hydrogen chloride, to convert the keto group of the zearalenane compound to a methylene group to obtain a zearalene compound having the structural formula 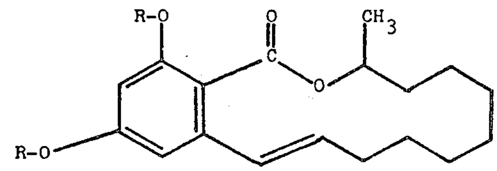 wherein R has the same meaning set forth above.

2. The process of claim 1 wherein the solvent is dioxane.

3. The process of claim 2 wherein R is hydrogen.

4. The process of claim 1 wherein the solvent is acetic anhydride.

5. The process of claim 4 wherein at least one R in the zearalenone compound is hydrogen and, during reduction, is converted to an acetyl group on the zearalene compound; the hydrogen halide is hydrogen chloride; and the reduction is conducted at a temperature from about −20°C. to +50°C.

6. The process of claim 5 wherein the zinc is employed in the solvent in an amount from about 1 to 20 parts by weight per part by weight of the zearalenone compound; the hydrogen halide is incorporated in the solvent in an amount from about 10 to 40 weight percent based on the weight of the solvent; and the solvent is employed in an amount from about 5 to 50 parts by weight per part by weight of the zearalenone compound.

7. The process of claim 6 wherein the zinc is employed in an amount from about 2.5 to 8 parts by weight per part by weight of the zearalenone compound.

8. The process of claim 7 wherein the reduction is conducted at a temperature from about −10°C. to +20°C.

9. The process of claim 5 wherein the zearalenone compound is 1'-trans-(10'S)-zearalenone; the zearalene compound resulting from the reduction is 2,4-diacetyl-1'-trans-(10'S)-zearalene which is subjected to hydrolysis conditions including an esterification agent in the presence of an esterification catalyst to produce zearalene.

10. The process of claim 9 wherein the esterification agent is a lower alkanol.

11. The process of claim 10 wherein the esterification catalyst is an alkali metal alkoxide.

12. The process of claim 11 wherein the catalyst is sodium methoxide.

13. The process of claim 10 wherein the esterification catalyst is an acid halide.

14. The process of claim 13 wherein the catalyst is hydrogen halide and the hydrolysis is conducted under reflux conditions.

* * * * *